US008026282B2

(12) United States Patent
Locke et al.

(10) Patent No.: US 8,026,282 B2
(45) Date of Patent: Sep. 27, 2011

(54) PHENOXYALKYLCARBOXYLIC ACID DERIVATIVES IN THE TREATMENT OF IRRITABLE BOWEL SYNDROME

(75) Inventors: Kenneth Walter Locke, Carlsbad, CA (US); Charles G. Smith, Rancho Sante Fe, CA (US); Takashi Kiyoizumi, San Diego, CA (US)

(73) Assignee: Medicinova, Inc., San Diego, CA (US)

( * ) Notice: Subject to any disclaimer, the term of this patent is extended or adjusted under 35 U.S.C. 154(b) by 0 days.

(21) Appl. No.: 12/776,032

(22) Filed: May 7, 2010

(65) Prior Publication Data
US 2010/0285074 A1  Nov. 11, 2010

Related U.S. Application Data

(62) Division of application No. 12/240,678, filed on Sep. 29, 2008, now Pat. No. 7,786,169, which is a division of application No. 11/115,225, filed on Apr. 27, 2005, now Pat. No. 7,429,617.

(60) Provisional application No. 60/565,527, filed on Apr. 27, 2004.

(51) Int. Cl.
*A61K 31/192* (2006.01)
(52) U.S. Cl. ........................................ 514/571
(58) Field of Classification Search ............... None
See application file for complete search history.

(56) References Cited

U.S. PATENT DOCUMENTS

| | | | |
|---|---|---|---|
| 4,428,935 A | 1/1984 | Myers | |
| 4,788,055 A | 11/1988 | Fischer et al. | |
| 4,816,264 A | 3/1989 | Phillips et al. | |
| 4,828,836 A | 5/1989 | Elger et al. | |
| 4,834,965 A | 5/1989 | Martani et al. | |
| 4,834,985 A | 5/1989 | Elger et al. | |
| 4,985,585 A | 1/1991 | Ohashi et al. | |
| 4,996,047 A | 2/1991 | Kelleher et al. | |
| 5,071,646 A | 12/1991 | Malkowska et al. | |
| 5,133,974 A | 7/1992 | Paradissis et al. | |
| 5,290,812 A | 3/1994 | Ohashi et al. | |
| 6,417,186 B1 | 7/2002 | Jahangir | |
| 7,064,146 B2 * | 6/2006 | Locke et al. | 514/545 |
| 7,728,169 B2 * | 6/2010 | Locke et al. | 562/431 |
| 2004/0266878 A1 | 12/2004 | Locke et al. | |
| 2004/0267041 A1 | 12/2004 | Locke et al. | |

FOREIGN PATENT DOCUMENTS
EP  0 332 109 A  9/1989
EP  0 495 485 A  7/1992

OTHER PUBLICATIONS

Tobin et al., Annals Allergy Asthma Immunology, 100(1) (Jun. 2010), 49-53 (Abstract).*

Ahluwalia et al., "Ovalbumin-induced neurogenic inflammation in the bladder of sensitized rats," *Br. J. Pharmacol.*, 124:190-6, 1998.
Chuang et al., "Intravesical Protamine sulfate and potassium chloride as a model for bladder hyperactivity," *Urology*, 61:664-70, 2003.
Henderson, "The Role of Leukotrienes in Inflammation," *Annals of Internal Medicine*, vol. 121, No. 9, pp. 684-697.
Fee, W.H., *Chest*, 122/4, Oct. 2002, p. 1497.
Bouchelouche, et al., *Journal of Urology*, (2001, 166(5), pp. 1734-1737 (abstract).
*The Merck Manual* (1999), 17th edition, pp. 307-315.
Monga, et al., *British Journal of Obstet. Gyn.* (Dec. 1997), 104(12): 1409-12 (abstract).
Whorwell, et al., *Gut*, (Sep. 1986), 27(9): 1014-7 (abstract).
Zaitsev, et al., "Modern Approach to Medicamentous Treatment of Interstitial Cystitis: Multimodal Approach," FARMATEKA, vol. 19, No. 61, 2002, Abstract, p. 34.
Holma,et al., "Acute Effects of the Cys-Leukotriene-1 Receptor Antagonist, Montelukast, on Experimental Colitis in Rats," *European Journal of Pharmacology*, vol. 429, No. 1-3, Oct. 19, 2001, pp. 309-318.
Nielsen,et al., "Effect of the Leukotriene LTD4LTE4 Antagonist, SR 2640, in Ulcerative Colitis: An Open Clinical Study," Prostaglandins Leukotrienes and Essential Fatty Acids, Churchill Livingstone, Edinburgh, vol. 42, No. 3, Mar. 1, 1991, pp. 181-184.
Riccioni, et al., "Brief Review: Advances in Therapy with Antileukotriene Drugs," Annals of Clinical and Laboratory Science, Institute for Clinical Science, Philadelphia, PA, vol. 34, No. 4, 2004, pp. 379-387.
Supplementary European Search Report mailed May 15, 2009 in European Application No. 05741700.8.
"Shin-Yakurigaku Souron" (New General Pharmaceutics), Apr. 10, 1987, revised 3rd edition, pp. 109-111.

* cited by examiner

*Primary Examiner* — Phyllis G. Spivack
(74) *Attorney, Agent, or Firm* — Gilberto M. Villacorta; Photon Rao; Foley & Lardner LLP

(57) ABSTRACT

A method of treating irritable bowel syndrome in a patient suffering therefrom comprising: administering an effective amount of a compound selected from compound 1, its metabolite 2 and pharmaceutically acceptable salts or esters thereof:

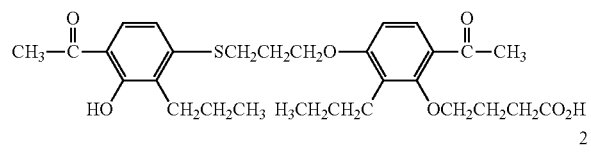

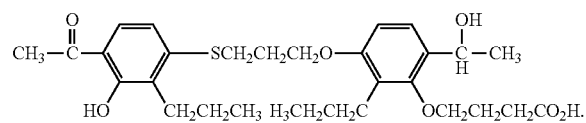

8 Claims, 7 Drawing Sheets

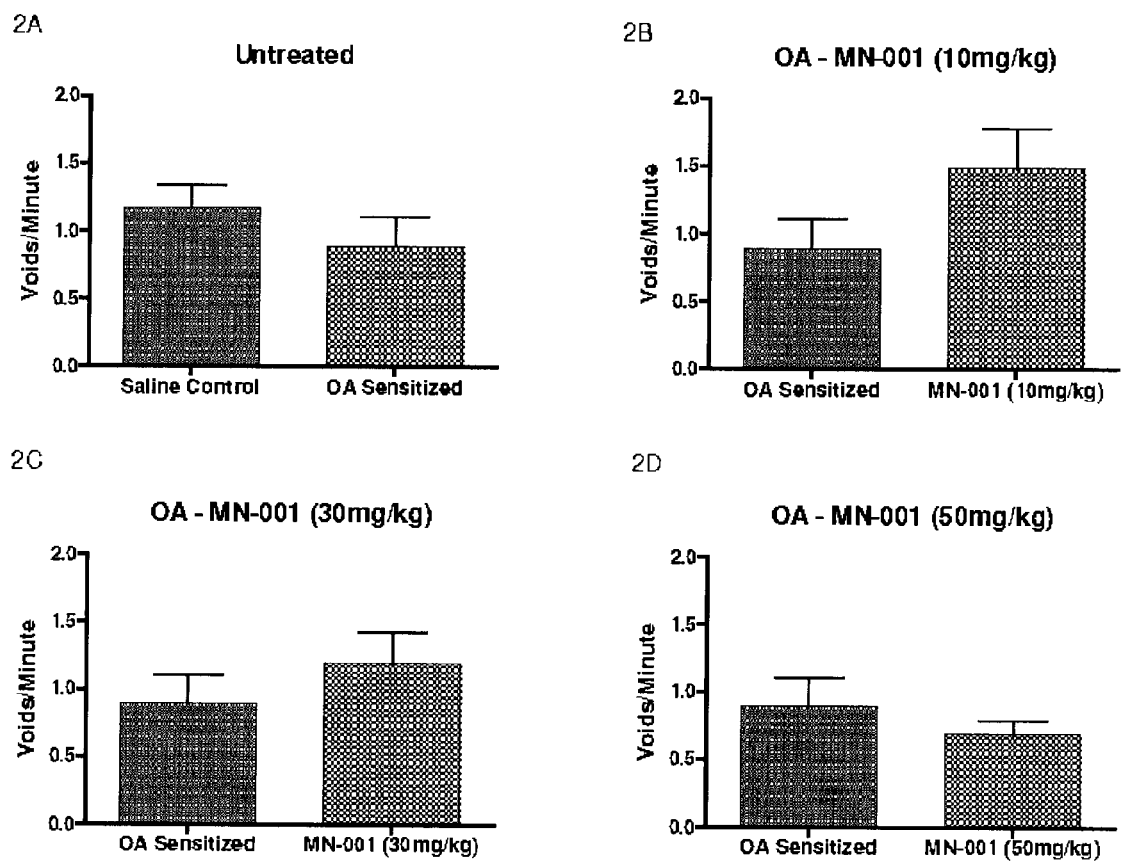
FIGS. 2A-2D. Voiding Frequency

FIGS. 3A-3D. Non Voiding Bladder Contractions
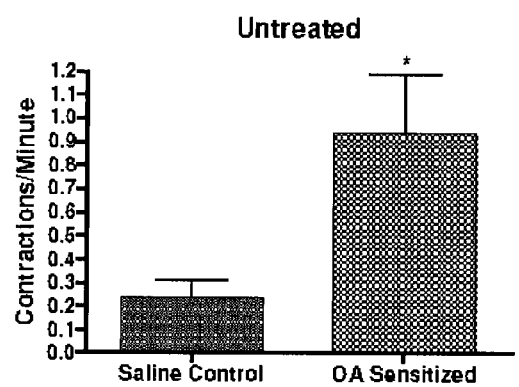
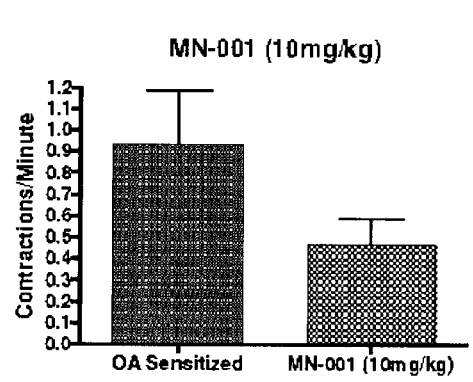
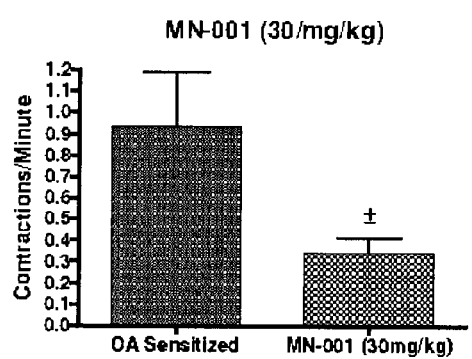
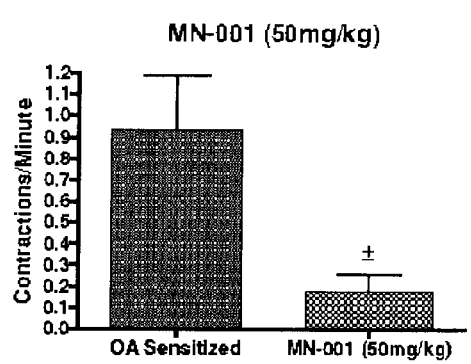

PHENOXYALKYLCARBOXYLIC ACID DERIVATIVES IN THE TREATMENT OF IRRITABLE BOWEL SYNDROME

CROSS REFERENCE TO RELATED APPLICATIONS

This application is a divisional of U.S. patent application Ser. No. 12/240,678, filed on Sep. 29, 2008, which is a divisional of U.S. patent application Ser. No. 11/115,225, filed on Apr. 27, 2005, which claims the benefit of U.S. Provisional Application No. 60/565,527, filed Apr. 27, 2004, the entire contents of which are incorporated herein by reference.

FIELD OF THE INVENTION

Method of treating interstitial cystitis irritable bowel syndrome, ulcerative colitis and other conditions involving inflammation.

BACKGROUND OF THE INVENTION

Interstitial cystitis (IC) is a chronic inflammation or irritation of the urinary bladder wall that is estimated to affect 700,000 people (approximately 90% female) in the United States. The primary symptoms of IC are urinary urgency, frequency, and often-severe pelvic and perineal pain. The similarity of the symptoms of IC with other bladder diseases, such as urinary tract infections (UTI), urethritis, urethral syndrome, trigonitis, prostatitis, dysuria, and nocturia has caused difficulty in the diagnosis of the disease. After other similar bladder diseases are ruled out and a cystoscopic examination of the bladder wall reveals characteristic signs of IC, including small petechial hemorrhages or larger Hunner's Ulcers, IC is usually diagnosed.

The etiology and pathogenesis of the transmural inflammation in IC are unclear. The diagnosis is one of exclusion, and the treatment is usually empiric. The symptoms of IC arise from a defect in the glycosaminoglycan (GAG) component of the mucin layer that covers and protects the bladder urothelium. A deficiency of this layer is thought to cause IC.

The GAG hypothesis is the basis for treating interstitial cystitis with glycosaminoglycan "replacements," such as sodium pentosan polysulfate and heparin or hyaluronic acid administered intravesically. Irritating substances in the urine may leak through the urothelium, causing inflammation, tissue irritation and injury, mast cell degranulation and sensory nerve depolarization, which result in the urinary urgency, frequency and pain of interstitial cystitis. Glycosaminoglycans are highly hydrophilic and protective. They maintain a stable layer of water between the urothelium and the bladder lumen, and prevent adhesion to and invasion of the urothelium by bacteria, microcrystals, ions, proteins and other substances in the urine.

Currently there is no permanent cure for IC in the majority of patients. Treatment of IC with drug therapy has been proven to be the most effective means of alleviating symptoms. Oral medications for IC include bladder-coating agents, antidepressants, antihistamines, antispasmodics, and anesthetics. The effectiveness of oral medications is limited by the circulating concentration of the drug in the blood stream. To address this limitation, many IC patients elect to undergo a procedure called urinary bladder instillation, in which a therapeutic solution is pumped into the bladder through a urethral catheter.

Proposed treatments include pentosan polysulfate, anti-inflammatory or immunosuppressant therapy, muscle relaxants, anti-histamines, and analgesics. Of these, only pentosan polysulfate (Elmiron) has been specifically approved by the FDA for IC. None of the proposed therapies, including pentosan polysulfate, which may take up to 6 months to work, is universally accepted or universally efficacious. There is no cure and no effective treatment that works for everyone; treatments are intended to relieve symptoms. Bladder distension, which is often part of diagnosis, is first line, because this treatment may ameliorate symptoms. Surgery is considered only in last resort and does not offer significant long term benefit.

The related conditions of irritable bowel syndrome and ulcerative colitis are also difficult to treat with existing therapeutic agents. These are nonspecific inflammatory diseases of the colon of unknown cause, characterized by diarrhea with discharge of mucus and blood, cramping abdominal pain, and inflammation and edema of the mucous membrane with patches of ulceration.

Without meaning to be limited by theory, we believe that a unique breadth of receptor sites can be blocked by compounds of the present invention. Few, if any, of the known inhibitors of inflammatory disease embody all of the following sites of activity in a single molecule: inhibition of 1) leukotriene synthesis, 2) leukotriene D-4 receptors, 3) leukotriene E-4 receptors, 4) cAMP PDE III, 5) cAMP PDE IV, 6) synthesis of thromboxane A-2, 7) eosinophil migration and 8) lymphocyte migration. The above mechanisms are involved and cooperate in different degrees and with different specificities among the wide variety of cells interacting in the so-called "inflammatory cascade," to produce a fission-like result. By blocking a wide variety of action sites, compounds 1 and 2 are expected to be effective for a wide array of illnesses that fall under the umbrella of "inflammatory diseases."

Since the biochemical messengers of inflammation cause an "explosive" type of reaction in the tissues, we suggest that the additive effects of the broad sites of action of the present compounds will result in high "multiplier" effects in amelioration of the urinary condition interstitial cystitis, as well as inflammatory disorders of the gastrointestinal tract, especially irritable bowel syndrome and ulcerative colitis.

SUMMARY OF THE INVENTION

An object of the invention is to provide a method of treating interstitial cystitis, comprising: administering to a patient in need of treatment for interstitial cystitis an effective amount of compound 1

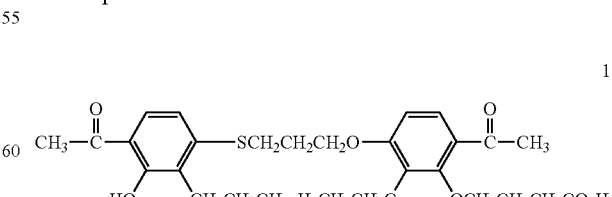

or a pharmaceutically acceptable salt thereof.

Another object of the invention is to provide a method of treating interstitial cystitis comprising, administering an effective amount of compound 2, a metabolite of compound 1:

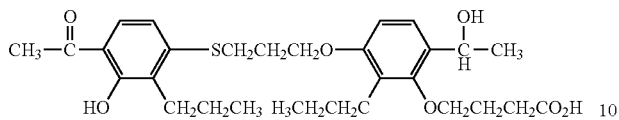

Another object of the invention is to provide a method of treating interstitial cystitis using an effective amount of compound 1 present in polymorphic Form A.

Another object of the invention is to provide a method of treating IBS/ulcerative colitis by administering an effective amount of compound 1 or 2.

BRIEF DESCRIPTION OF THE FIGURES

FIGS. 2A-2D. Voiding frequency in (A) Control and OA sensitized rats; (B) before and after Compound 1 (10 mg/kg) treatment; (C) before and after Compound 1 (30 mg/kg) treatment; (D) before and after Compound 1 (50 mg/kg) treatment.

FIGS. 3A-3D. NVCs in (A) Control and OA sensitized rats; (B) before and after Compound 1 (10 mg/kg) treatment; (C) before and after Compound 1 (30 mg/kg) treatment; (D) before and after Compound 1 (50 mg/kg) treatment. An * denotes significance when compared to group 1. A ± denotes significance when compared to group 2.

DETAILED DESCRIPTION OF THE INVENTION

Figure 1A:
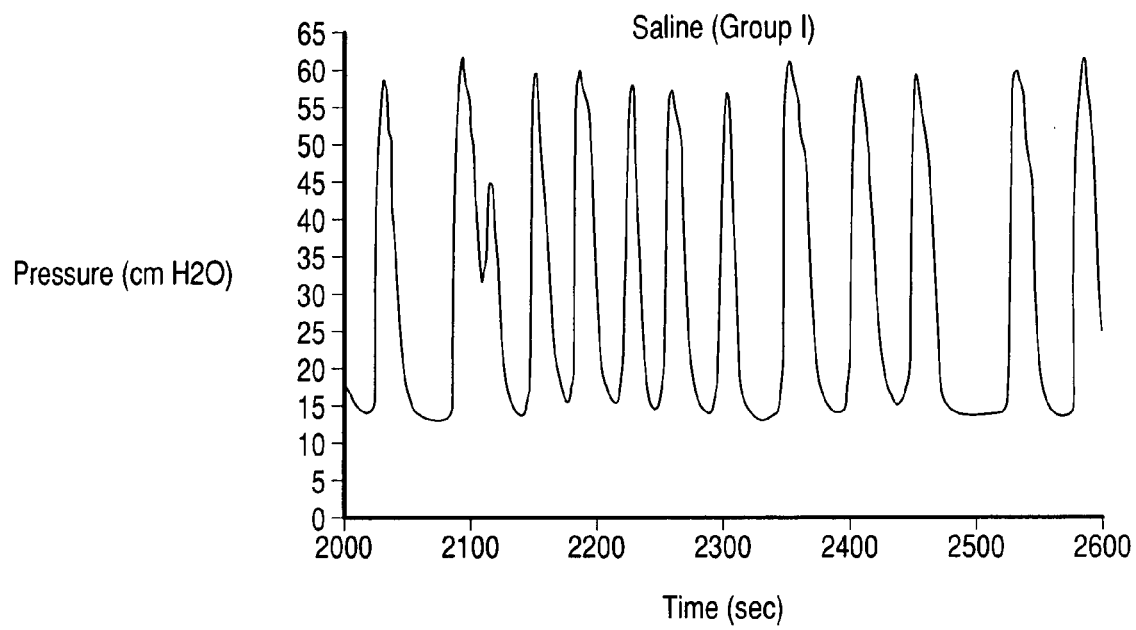
FIGS. 1A-1E. Representative bladder CMGs during (A) saline infusion, (B) OA infusion, (C). OA infusion after Compound 1 (10 mg/kg); (D) OA infusion after Compound 1 (30 mg/kg); (E) OA infusion after Compound 1 (50 mg/kg).
Figure 1B:
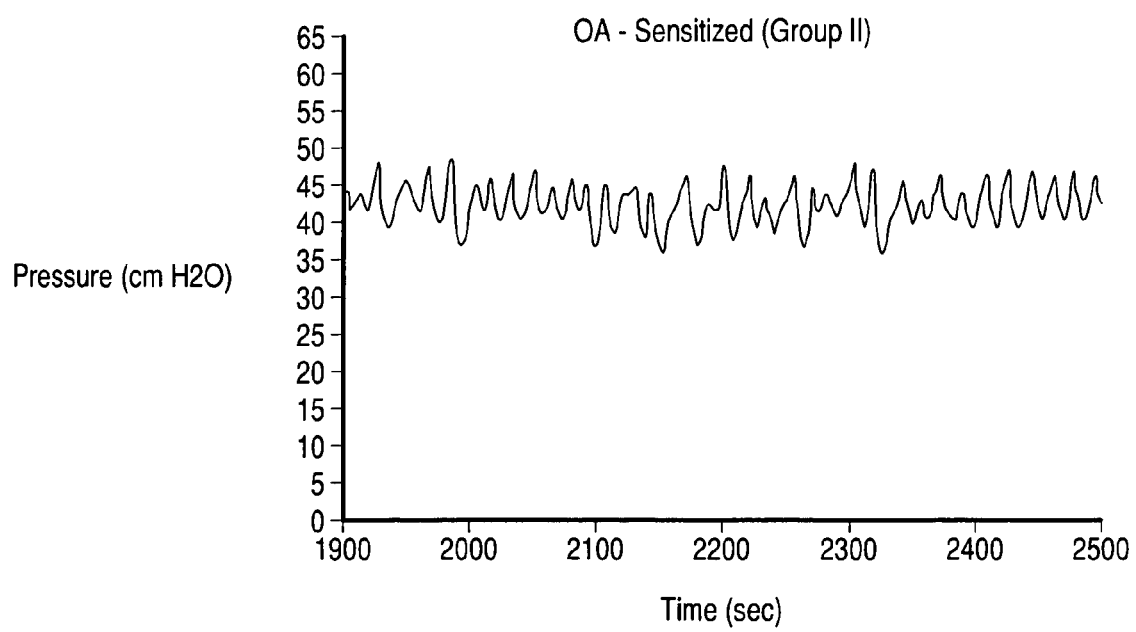
Figure 1C:
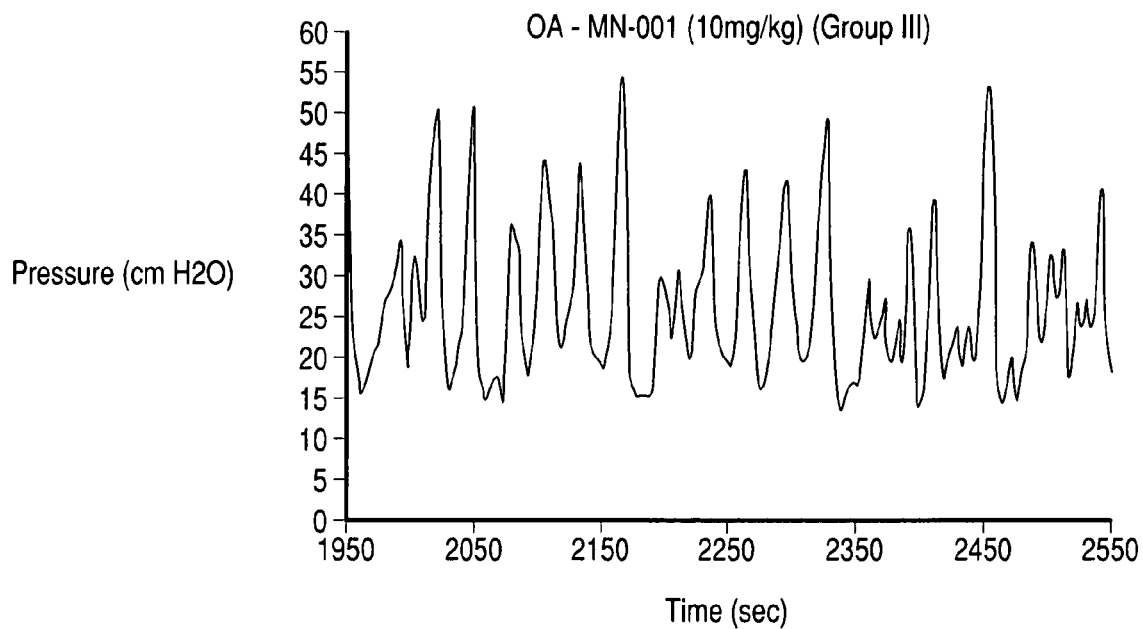
Figure 1D:
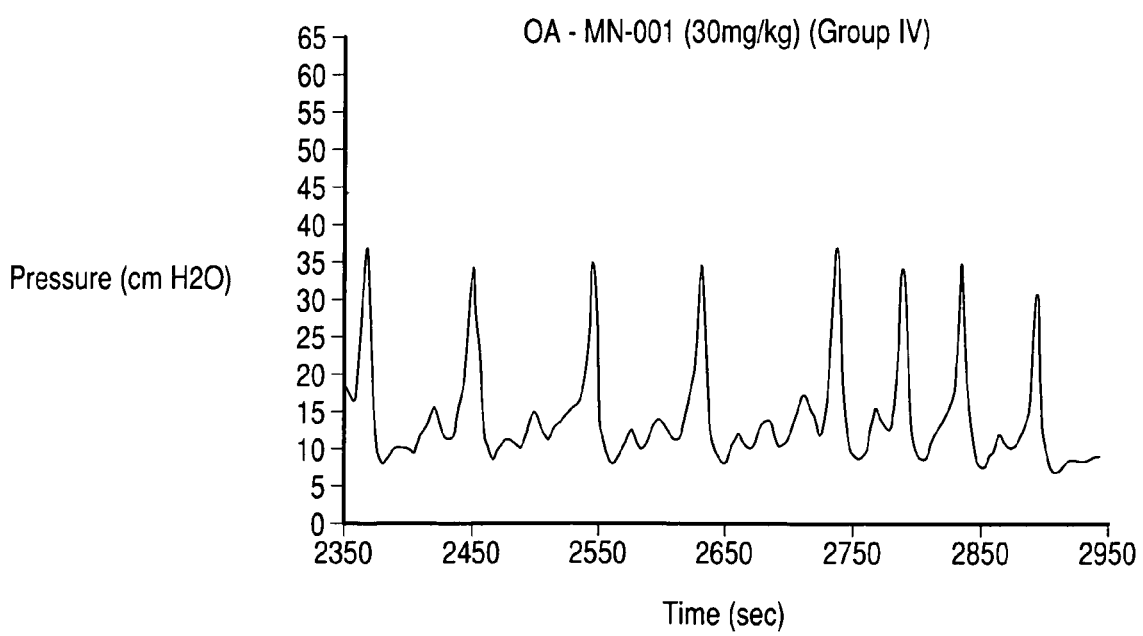
Figure 1E:
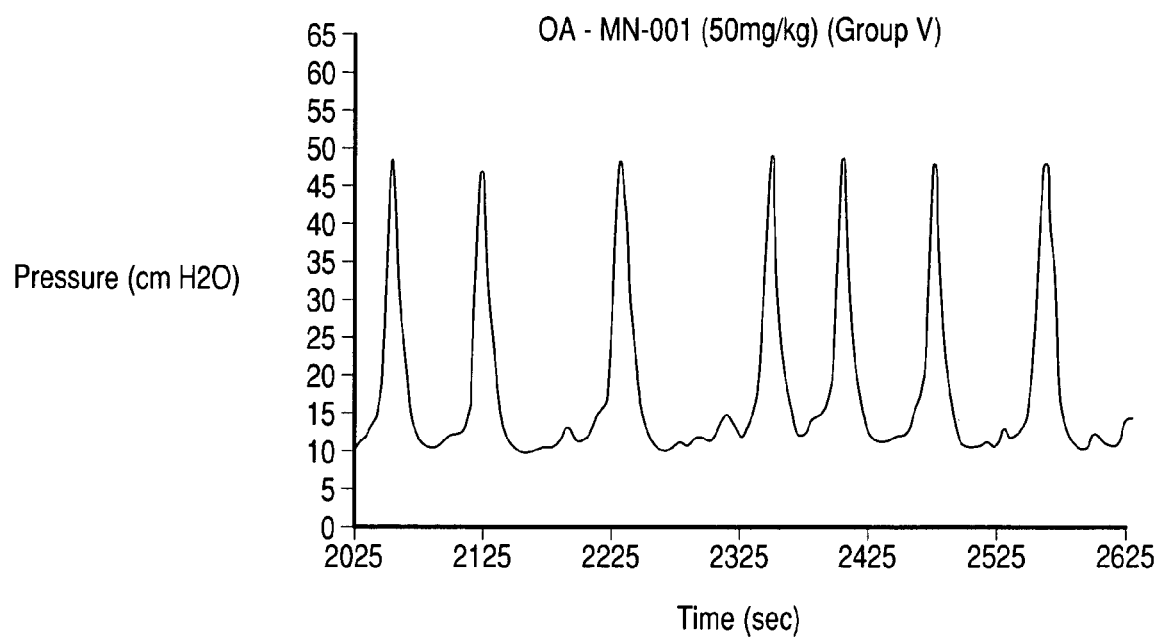

The compound 4-[6-acetyl-3-[3-(4-acetyl-3-hydroxy-2-propylphenylthio)propoxy]-2-propylphenoxy]butyric acid (1) (MN-001), and its pharmaceutically acceptable salts and protected prodrug forms, are orally active for treatment of interstitial cystitis.

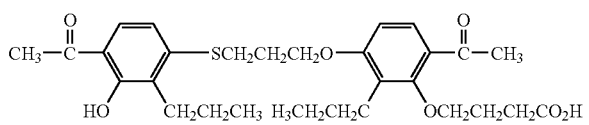

The compound of formula 2 (MN-002), a metabolite of compound 1, is the dominant form in human plasma. It is also active for treatment of interstitial cystitis and can exist as two stereoisomers. The in vitro potency of the separated optical isomers of compound 2 are nearly identical against leukotrienes. Similarly, the acute toxicity (LD50) of both optical isomers is about the same. The isomers can be isolated by chiral chromatography methods. The racemate has been tested in long-term rodent and dog safety studies. Pharmacologically, the in vivo activity of the (−)-isomer and the racemate are similar. Pharmacokinetically, the isomers behave similarly in rats and dogs, with no evidence of interconversion.

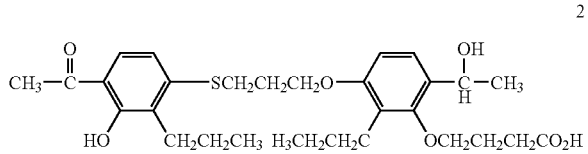

The synthesis and biological activity of many phenoxyalkylcarboxylic acid derivatives, including compounds 1 and 2, are described by Ohashi et al. in U.S. Pat. Nos. 4,985,585 and 5,290,812, which are incorporated herein by reference.

Compound 1 may be prepared by reacting a phenol of formula 3:

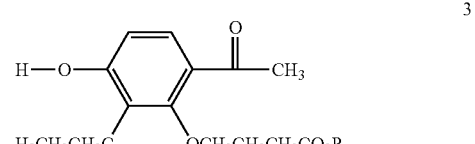

wherein R is an acid protecting group, such as methyl or ethyl, with the bromo compound of formula 4 to give compound 5:

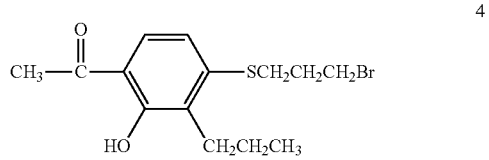

in an organic solvent, for example acetone, methylethylketone, diethylketone or dimethylformamide. The nucleophilic displacement reaction may be conducted from below room temperature up to the reflux temperature of the solvent, in the presence of an inorganic base, e.g., potassium carbonate or sodium carbonate. The addition of potassium iodide is also recommended. Analogues of compound 4 having alternative leaving groups, such as chloro and tosylate, may be used to effect this coupling reaction.

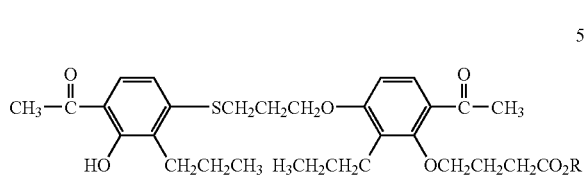

Removal of the protecting group in 5 by alkaline ester hydrolysis and extractive work-up gives compound 1 as a white solid.

Recrystallization of the white solid under controlled conditions gives an essentially pure polymorph, designated as Form A crystals (e.g., 90% or more, preferably at least 95% Form A). Polymorphic Form A and processes for producing it are described in U.S. patent application Ser. Nos. 10/601,861 and 10/601,862, both filed Jun. 24, 2003; which are incorporated herein by reference. All polymorphic forms of compound 1 are active, but Form A is preferred. The solubility and the bioavailability of this polymorph, identified as orthorhombic crystals, is superior to the other polymorphs and thus Form A offers improved solid formulations.

Form A crystals can be obtained by dissolving compound 1 in 5 to 10 parts by weight of ethanol at 25-40° C. to give a yellow to orange solution. The ethanol solution is charged with 1-10 parts of water and agitated at 20-25° C. for about 15-60 minutes and then at 5-10° C. for an additional period of 1-4 hours, preferably 2.0-3.0 hours, resulting in an off-white suspension. To this suspension is added 5-15 parts of water and the mixture is agitated at 5-10° C. for an additional 1-4 hours, preferably 1.5-2.0 hours. A solid, white to off-white product is isolated by vacuum filtration and the filter cake is washed with water and dried in a vacuum at 25-40° C. for 12-24 hours.

Additional synthetic methods are shown below, where DHPA is 2,4-dihydroxy-3-propylacetophenone and CHPA is 4-(3-chloropropoxy)-2-hydroxyl-3-propylacetophenone.

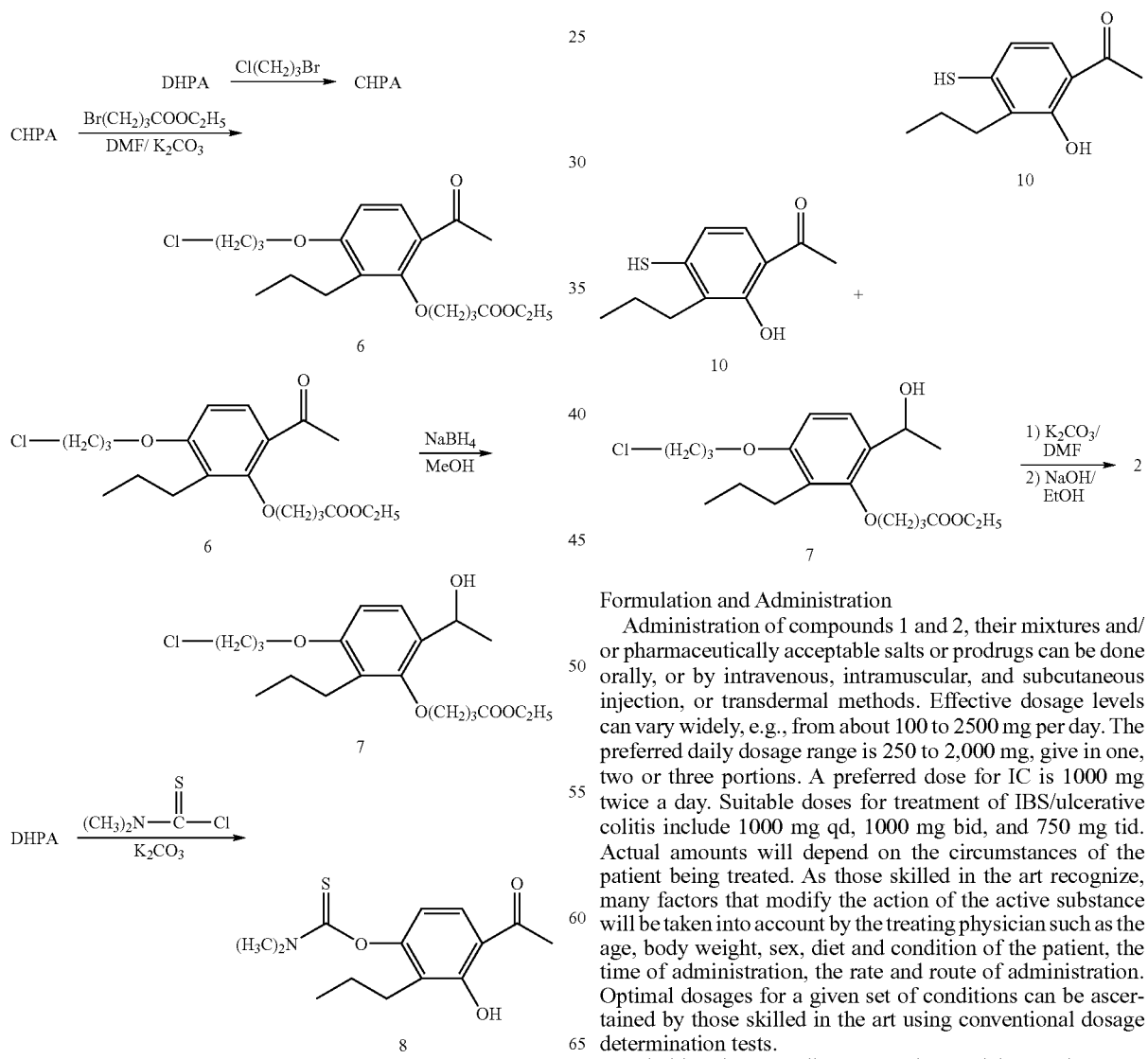

Formulation and Administration

Administration of compounds 1 and 2, their mixtures and/or pharmaceutically acceptable salts or prodrugs can be done orally, or by intravenous, intramuscular, and subcutaneous injection, or transdermal methods. Effective dosage levels can vary widely, e.g., from about 100 to 2500 mg per day. The preferred daily dosage range is 250 to 2,000 mg, give in one, two or three portions. A preferred dose for IC is 1000 mg twice a day. Suitable doses for treatment of IBS/ulcerative colitis include 1000 mg qd, 1000 mg bid, and 750 mg tid. Actual amounts will depend on the circumstances of the patient being treated. As those skilled in the art recognize, many factors that modify the action of the active substance will be taken into account by the treating physician such as the age, body weight, sex, diet and condition of the patient, the time of administration, the rate and route of administration. Optimal dosages for a given set of conditions can be ascertained by those skilled in the art using conventional dosage determination tests.

Suitable salts are sodium, potassium, calcium and magnesium, with sodium being preferred. Suitable prodrug forms include carboxylic esters which are readily hydrolyzable in vivo and release the active acid in vivo. An example of such a protecting group is disclosed in U.S. Pat. No. 4,428,935, incorporated herein by reference.

The following protecting group is described in U.S. Pat. No. 4,428,935:

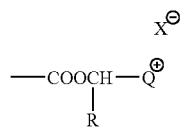

wherein

R is hydrogen;

Q is selected from the group consisting of

N(R¹)(R²)(R³) wherein R¹, R² and R³ are each alkyl having 1-4 carbon atoms, hydroxyalkyl having 1-4 carbon atoms, alkoxycarbonylalkyl wherein the alkyl has 1-4 carbon atoms and the alkoxy has 1-4 carbon atoms or aminocarbonylalkyl wherein the alkyl has 1-4 carbon atoms, N-alkyl-morpholyl wherein the alkyl has 1-4 carbon atoms, N-alkyl-piperidyl wherein the alkyl has 1-4 carbon atoms or N-alkyl-pyrrolidyl wherein the alkyl has 1-4 carbon atom, and those groups substituted at a ring position with alkyl having 1-4 carbon atoms, aminocarbonyl, hydroxyl or alkoxycarbonyl wherein the alkoxy has 1-4 carbon atoms, bicyclo [2.2.2]1-,4-diazaoctanyl and those substituted with alkyl having 1-4 carbon atoms, aminocarbonyl, hydroxyl or alkoxycarbonyl wherein the alkoxy has 1-4 carbon atoms, pyridyl, alkylpyridyl wherein the alkyl has 1-4 carbon atoms, dialkylpyridyl wherein each alkyl has 1-4 carbon atoms, trialkylpyridyl wherein each alkyl has 1-4 carbon atoms, halopyridyl, cyanopyridyl, nitropyridyl, aminocarbonylpyridyl, N-alkylaminocarbonylpyridyl wherein the alkyl has 1-4 carbon atoms, N,N-dialkylaminocarbonylpyridyl wherein each alkyl has 1-4 carbon atoms, alkoxycarbonylpyridyl wherein the alkoxy contains 1-4 carbon atoms, or N,N-dialkylaminopyridyl wherein each alkyl has 1-4 carbon atoms, and quinolyl or N-alkylimidazolyl wherein the alkyl has 1-4 carbon atoms; and X⁻ is a pharmaceutically-acceptable anion.

The compounds of the present invention can be formulated in any pharmaceutically acceptable form, including liquids, powders, creams, emulsions, pills, troches, suppositories, suspensions, solutions, and the like. Therapeutic compositions containing compounds 1 and 2, their mixtures and/or pharmaceutically acceptable salts will ordinarily be formulated with one or more pharmaceutically acceptable ingredients in accordance with known and established practice. In general, tablets are formed utilizing a carrier such as modified starch, alone or in combination with 10% by weight of carboxymethyl cellulose (Avicel). The formulations are compressed at from 1,000 to 3,000 pounds pressure in the tablet-forming process. The tablets preferably exhibit an average hardness of about 1.5 to 8.0 kp/cm², preferably 5.0 to 7.5 kp/cm². Disintegration time varies from about 30 seconds to about 15 or 20 minutes. The following examples give specific embodiments of the invention but should not be construed as limiting its scope.

Formulations for oral use can be provided as hard gelatin capsules wherein the phenoxyalkylcarboxylic acid, mixtures thereof or pharmaceutically acceptable salts are mixed with an inert solid diluent such as calcium carbonate, calcium phosphate or kaolin, or as soft gelatin capsules in which the compounds are mixed with an oleaginous medium, e.g., liquid paraffin or olive oil. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

Aqueous suspensions can contain the compounds, their mixtures and/or pharmaceutically acceptable salts in admixture with pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkaline oxide with fatty acids, e.g., polyoxyethylene stearate, or condensation products of ethylene oxide with long chain aliphatic alcohols, e.g, heptadecaethylene-oxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monoleate. Such aqueous suspensions can also contain one or more preservatives, e.g., ethyl-or-n-propyl-p-hydroxy benzoate, one or more coloring agents, one or more flavoring agents and one or more sweetening agents, such as sucrose, saccharin or sodium or calcium cyclamate.

Dispersible powders and granules suitable for preparation of an aqueous suspension by the addition of water provide the compounds of formulas 1 and 2, their mixtures and/or pharmaceutically acceptable salts in admixture with a dispersing or wetting agent, suspending agent and one or more preservatives. Suitable dispersing or wetting agents and suspending agents are exemplified by those already mentioned above. Additional excpients, e.g., sweetening, flavoring and coloring agents, can also be present. Syrups and elixirs can be formulated with sweetening agents, for example glycerol, sorbitol or sucrose. Such formulations can also contain a demulcent, a preservative and flavoring and coloring agents.

The present invention can be administered in sustained release dosage form, of which many kinds are known, e.g., as described in U.S. Pat. Nos. 4,788,055; 4,816,264; 4,828,836; 4,834,965; 4,834,985; 4,996,047; 5,071,646; and, 5,133,974, the contents of which are incorporated by reference herein.

It is also within the scope of this invention to administer the subject compounds concurrently with, or after administration of any other known pharmacologically active agent useful for treating urinary incontinence. Such agents include, anticholinergics such as oxybutynin, atropine, propantheline, terodiline, and dicyclomine; sympathomimetics such as ephedrine, pseudoephedrine, epinephrine, and phenylpropanolamine; tricyclic antidepressants such as imipramine, doxepin, and amitriptyline; estrogens or estrogen-related compounds having estrogen-like activity such as estradiol, and estrone; and antispasmodics or direct acting bladder smooth muscle relaxants such as flavoxate. For a detailed discussion of these pharmacologically active agents, reference may be made to "Goodman and Gillman's Pharmacological Basis of Therapeutics", Goodman et al., eds. 7th ed., 1985, Macmillan and Company, New York.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), (for example, dichlorodifluoromethane, trichlorofluoromethane, or dichlorotetrafluoroethane), carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. A common type of controlled-release formulation that may be used for the purposes of the present invention comprises an inert core, such as a sugar sphere, coated with an inner drug-containing layer and an outer membrane layer controlling drug release from the inner layer.

The cores are preferably of a water-soluble or swellable material, and may be any such material that is conventionally used as cores or any other pharmaceutically acceptable water-soluble or water-swellable material made into beads or pellets. The cores may be spheres of materials such as sucrose/starch (Sugar Spheres NF), sucrose crystals, or extruded and dried spheres typically comprised of excipients such as microcrystalline cellulose and lactose.

The substantially water-insoluble material in the first layer is generally a "GI insoluble" or "GI partially insoluble" film forming polymer (dispersed or dissolved in a solvent). As examples may be mentioned ethyl cellulose, cellulose acetate, cellulose acetate butyrate, polymethacrylates such as ethyl acrylate/methyl methacrylate copolymer (Eudragit NE-30-D) and ammonio methacrylate copolymer types A and B (Eudragit RL30D and RS30D), and silicone elastomers. Usually, a plasticizer is used together with the polymer. Exemplary plasticizers include: dibutylsebacate, propylene glycol, triethylcitrate, tributylcitrate, castor oil, acetylated monoglycerides, acetyl triethylcitrate, acetyl butylcitrate, diethyl phthalate, dibutyl phthalate, triacetin, fractionated coconut oil (medium-chain triglycerides).

The second layer containing the active ingredient may be comprised of the active ingredient (drug) with or without a polymer as a binder. The binder, when used, is usually hydrophilic but may be water-soluble or water-insoluble. Exemplary polymers to be used in the second layer containing the active drug are hydrophilic polymers such as polyvinylpyrrolidone (PVP), polyalkylene glycol such as polyethylene glycol, gelatine, polyvinyl alcohol, starch and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, carboxymethylhydroxyethyl cellulose, acrylic acid polymers, polymethacrylates, or any other pharmaceutically acceptable polymer. The ratio of drug to hydrophilic polymer in the second layer is usually in the range of from 1:100 to 100:1 (w/w).

Suitable polymers for use in the third layer, or membrane, for controlling the drug release may be selected from water-insoluble polymers or polymers with pH-dependent solubility, such as, for example, ethyl cellulose, hydroxypropylmethyl cellulose phthalate, cellulose acetate phthalate, cellulose acetate trimellitate, polymethacrylates, or mixtures thereof, optionally combined with plasticizers, such as those mentioned above.

Optionally, the controlled release layer comprises, in addition to the polymers above, another substance(s) with different solubility characteristics, to adjust the permeability, and thereby the release rate, of the controlled release layer. Exemplary polymers that may be used as a modifier together with, for example, ethyl cellulose include: HPMC, hydroxyethyl cellulose, hydroxypropyl cellulose, methylcellulose, carboxymethylcellulose, polyethylene glycol, polyvinylpyrrolidone (PVP), polyvinyl alcohol, polymers with pH-dependent solubility, such as cellulose acetate phthalate or ammonio methacrylate copolymer and methacrylic acid copolymer, or mixtures thereof. Additives such as sucrose, lactose and pharmaceutical grade surfactants may also be included in the controlled release layer, if desired.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa. Representative pharmaceutical formulations containing a compound of the present invention are described in the Examples.

The following table reports data from a comprehensive biochemical evaluation of compounds 1 and 2, showing these drugs can hit several inflammatory chemical mediators simultaneously, which appears to be the basis for their unique therapeutic activities. TNF alpha has been suggested as a probable disease provocateur in arthritis, heart disease, IBD and cachexia. Likewise, the cAMP/cGMP system is implicated in a wide number of diseases or disorders and are expected to respond to treatment with compounds 1 and 2 including prostatitis, IBS/IBD, and multiple sclerosis, etc.

| Biochemical Assay | Species | $IC_{50}$ ($K_i$) (µM) MN-001 | $IC_{50}$ ($K_i$) (µM) MN-002 |
|---|---|---|---|
| LTC4 Synthetase | Gp | 24.7 | 18.3 |
| 5-LO | Hu | 1.11 | 1.61 |
| PDE1 | Bov | 0.741 | 3.08 |
| PDE2 | Hu | 3.43 | 3.38 |
| PDE3 | Hu | 0.567 | 1.68 |
| PDE4 | Hu | 0.639 | 0.303 |
| PDE5 | Hu | 12.7 | 8.47 |
| PDE6 | Bov | 2.05 | 1.73 |
| PLA2-I | Pig | 142 | 248 |
| PLC | Ba | 0.59 | 5.13 |
| Adrenergic α2B | Hu | 2.81 (1.28) | 1.6 (0.732) |
| Adrenergic β3 | Hu | 4.63 (3.47) | 1.1 (0.821) |
| Adrenergic, NE Transporter | Hu | 3.5 (3.47) | 2.05 (2.03) |
| LTB4 | Hu | 9.02 (2.29) | — |
| LTD4 | Gp | 6.36 (3.18) | 5.35 (2.67) |
| Melanocortin MC5 | Hu | 2.58 (2.42) | 1.82 (1.71) |
| Opiate δ | Hu | 1.04 (0.365) | 3.03 (1.07) |
| Thromboxane A2 | Hu | 3.37 (2.2) | 3.89 (2.54) |

Ba = *bacillus cereus*,
— = not tested

The following examples are illustrative of the present invention and should not be construed as limiting.

EXAMPLE 1

Synthesis of ethyl 4-[6-acetyl-3-[3-(4-acetyl-3-hydroxy-2-propylphenylthio)-propoxy]-2-propyl phenoxy]butyrate To a stirred mixture of ethyl 4-(6-acetyl-3-hydroxy-2-propylphenoxy)butyrate (1.6 g), potassium iodide (0.5 g) and potassium carbonate (1.45 g) in acetone (30 ml) was added drop wise a solution of 4-(3-bromopropylthio)-2-hydroxy-3-propylphenyl-ethanone (1.9 g) in acetone (10 ml) with heating to reflux. After refluxing six hours the mixture was cooled to room temperature and inorganic materials were separated by filtration. The filtrate was concentrated and the residue was separated and purified by silica-gel column chromatography (eluting with benzene:ethyl acetate=9:1) to give the title compound as crude crystals (2.1 g, 72.4%) which were recrystallized from ethanol to give colorless crystals, mp 65-66° C.

EXAMPLE 2

Synthesis of 4-[6-acetyl-3-[3-(4-acetyl-3-hydroxy-2-propylphenylthio)propoxy]-2-propylphenoxy]butyric acid To a mixture of ethyl 4-[6-acetyl-3-[3-(4-acetyl-3-hydroxy-2-propylphenylthio)propoxy]-2-propylphenoxy]butyrate (2.1 g) in ethanol (10 ml) was added a solution of sodium hydroxide (0.26 g) dissolved into water (10 ml). After heating on a hot water bath for 5 minutes, the mixture was cooled by adding ice-water and was made acidic by addition of hydrochloric acid, followed by extraction with ethyl acetate. The organic layer was washed with water, dried over sodium sulfate and concentrated. The resultant residue was separated and purified by silica-gel column chromatography (eluting with ethanol:methylene chloride=3:100) to give the title compound (1.3 g, 65.2%) as colorless crystals, mp 79-81° C.

EXAMPLE 3

Bulk crystallization procedure for obtaining orthorhombic polymorph, crystal type V (Form A).

Off-white solid compound (1) 34 g was dissolved in 204 mL (6 parts wrt mass of dry filter cake) of ethanol (40° C.) giving a yellow to orange solution. With moderate agitation, the ethanol solution was charged with 43 mL (1.3 parts) of water. The reaction mixture was cooled to 20-25° C. and agitated at 20-25° C. for about 15 minutes and then at 10-15° C. for an additional period of 1-2 hours, appearing as an off-white suspension.

To the resulting suspension was then charged 364 mL (10.7 parts) of water and the mixture was agitated at 5-10° C. for an additional 1-2 hours. A solid, white to off-white product was isolated by vacuum filtration. The filter cake was washed with 2×30 mL of water. The off white solid was dried in a vacuum at 35-40° C. for 24 hours.

EXAMPLE 4

In general, wet granulation tablets were prepared with a binding solution comprised of an aqueous solution of hydroxypropylcellulose. Granulation was performed with a high shear granulator, the resultant wet mass was fluid bed dried, milled, blended with extragranular excipients to aid disintegration, flow and compressibility, and subsequently tabletted on a tablet press. These core tablets were film coated to standardize appearance and to improve compliance (i.e. ease of swallowing). Excipients included, but were not limited to croscarmellose sodium, magnesium stearate, hydroxypropylcelluse, hydroxypropylmethylcellulose, lactose, glyceryl behenate, polyvinylpyrrolidine, mannitol, titanium dioxide and microcrystalline cellulose.

EXAMPLE 5

In general, the dry granulation formulation was formed by dry blending (in a tumble blender or high shear mixer) a portion of the binding, disintegration and lubrication powders. This dry powder blend was formed into granules through the use of a roller compactor equipped with an oscillating (shear) granulator. The ss mesh screen, gap width, gap force, roller speed and granulator speeds were defined to optimize the formulation physical parameters as apparent to those skilled in the art of pharmaceutical processing. Excipients included, but were not limited to croscarmellose sodium, magnesium stearate, hydroxypropylcelluse, hydroxypropylmethylcellulose, lactose, glyceryl behenate, polyvinylpyrrolidine, mannitol, titanium dioxide and microcrystalline cellulose.

EXAMPLE 6

Specific Formulation for Dry Granulation

| No. | Ingredient | Prototype 1 (mg/tablet) | Prototype 2 (mg/tablet) |
| --- | --- | --- | --- |
| 1 | Compound (1) (Form A) | 250 | 250 |
| 2 | Lactose regular/fast flow | 7.5 | — |
| 3 | Microcrystalline cellulose PH101 | 31 | 31 |
| 4 | Croscarmellose sodium | 20 | 20 |
| 5 | Hydroxypropylcellulose | 80 | — |
| 6 | Magnesium stearate | 2.0 | — |
| 7 | Hydroxypropylmethylcellulose 2910 | 8.0 | — |
| 8 | Titanium Dioxide | 1.0 | — |
| 9 | Carnauba wax | 0.5 | 0.5 |
| 10 | Polyvinylpyrrolidone | — | 85 |
| 11 | Mannitol | — | 3.5 |
| 12 | Glyceryl behenate | — | 2.0 |
| 13 | Opadry II (white) | — | 8.0 |
|  | Total | 400 mg | 400 mg |

EXAMPLE 7

Specific Formulations for Wet Granulation

| No. | Ingredient | Prototype 3 (mg/tablet) | Prototype 4 (mg/tablet) |
| --- | --- | --- | --- |
| 1 | Compound (1) (Form A) | 250 | 250 |
| 2 | Lactose regular/fast flow | 7.5 | — |
| 3 | Microcrystalline cellulose PH101 | 32 | 32 |
| 4 | Croscarmellose sodium | 25 | 25 |
| 5 | Hydroxypropylcellulose | 25 | — |
| 6 | Magnesium stearate | 2.0 | — |
| 7 | Hydroxypropylmethylcellulose 2910 | 7.0 | — |
| 8 | Titanium Dioxide | 1.0 | — |
| 9 | Carnauba wax | 0.5 | 0.5 |
| 10 | Polyvinylpyrrolidone | — | 30 |
| 11 | Mannitol | — | 3.5 |

-continued

| No. | Ingredient | Prototype 3 (mg/tablet) | Prototype 4 (mg/tablet) |
| --- | --- | --- | --- |
| 12 | Glyceryl behenate | — | 2.0 |
| 13 | Opadry II (white) | — | 7.0 |
|  | Total | 350 mg | 350 mg |

EXAMPLE 8

A 35-year-old female complains of suffering symptoms associated with interstitial cystitis (IC), including gastrointestinal symptoms of diarrhea, bloating and pain. In an effort to alleviate these symptoms, a tablet containing 1000 mg of compound (1) (Form A) is administered orally to this female patient twice daily for at least 2 months. After this time period, this patient reports positive effects, including a reduction in the symptoms she complained of. Similar positive results are observed for other patients complaining of the same or similar symptoms attributable to IC.

EXAMPLE 9

A 35-year-old male complains of symptoms associated with IBS/ulcerative colitis, including diarrhea with discharge of mucus and blood, cramping abdominal pain, and inflammation and edema of the mucous membrane with patches of ulceration. The patient is treated with tablets containing 750 mg of compound (1), three times per day, for at least two months. After this time period, he reports positive effects, including a reduction in the symptoms complained of. Similar positive results are observed for other patients complaining of the same or similar symptoms attributable to IBS or ulcerative colitis.

EXAMPLE 10

Previous reports have demonstrated that intravesical instillation of ovalbumin in sensitized guinea pigs increases bladder contractions. See, Ahluwalia A, Giuliani S, Scotland R and Maggi C A: Ovalbumin-induced neurogenic inflammation in the bladder of sensitized rats. Br. J. Pharmacol. (1998) 124:190-6. Compound 1 (1), exhibiting anti-inflammatory activity with mast cell stabilizing potential, has been shown to be beneficial in suppressing ovalbumin-induced bladder contractions. The protective potential of 1 in a rat model of inflammation-induced bladder hyperactivity has been evaluated, as described below. This rat model serves as an animal model for interstitial cystitis, irritable bowel syndrome, ulcerative colitis, and potentially other inflammatory conditions.

Methods:

A. Sensitization of Rats:

Sprague-Dawley rats (n=50; 200±250 g) were utilized for this study. The animals were divided into 5 groups (n=10). The first group served as the control and the second group was sensitized with ovalbumin (OA). The third, fourth, and fifth groups were also sensitized as described but subjected to oral gavaging with Compound 1 prior to acute ovalbumin challenge.

Sensitization of the animals was accomplished with an intraperitoneal injection of a mixture of 1 mg OA and 100 mg aluminum hydroxide suspended in 1 mL of saline. Fourteen days later, these sensitized rats were anaesthetized with a subcutaneous injection of urethane (1.2 g/kg) for intravesical OA (10 mg/mL) administration and evaluation of bladder hyperactivity. The animals in group 1 received saline (control), group 2 animals received about 2 mL of OA (10 mg/mL OA in sterile saline) and animal groups 3-5 animals received oral 1 (10, 30, 50 mg/kg in gum acacia suspension) 60 minutes prior to acute OA challenge (2 mL of 10 mg/mL OA).

B. Evaluation of Bladder Overactivity:

All animals were subjected to evaluation of bladder hyperactivity. Briefly, a 1 cm incision was made along the centerline of the lower ventral abdomen. The bladder was exteriorized, and catheterized by means of a polyethylene tube (PE 50, Clay Adams) inserted into the bladder dome and sutured in place using a 2-0 braided silk suture. The bladder was returned to the abdomen, with the catheter line escaping through the incision. The catheter was then connected to a pressure transducer (UFI, Morro Bay, Calif.) and in turn, connected to an infusion pump (Harvard Apparatus, MA). During the continuous filling bladder cystometry, the pressure was recorded with the transducer using the program LabVIEW (National Instruments, TX).

For cystometry (See, Chuang Y C, Chancellor M B, Seki S, Yoshimura N, Tyagi P, Huang L, Lavelle J P, De Groat W C and Fraser M O: Intravesical protamine sulfate and potassium chloride as a model for bladder hyperactivity. Urology (2003) 61:664-70), the bladder was first infused with warm 0.9% saline (37° C.) at 40 µL/min (2.4 mL/hr) and at least 20 minutes of stable voiding cycles were recorded during infusion. This process was followed by intravesical infusion of OA (10 mg/mL) and bladder contractions were recorded. Frequency of contractions (voids), inter-contractile interval (ICI), and non-voiding contractions (NVC) were calculated from these recordings.

Figure 4:
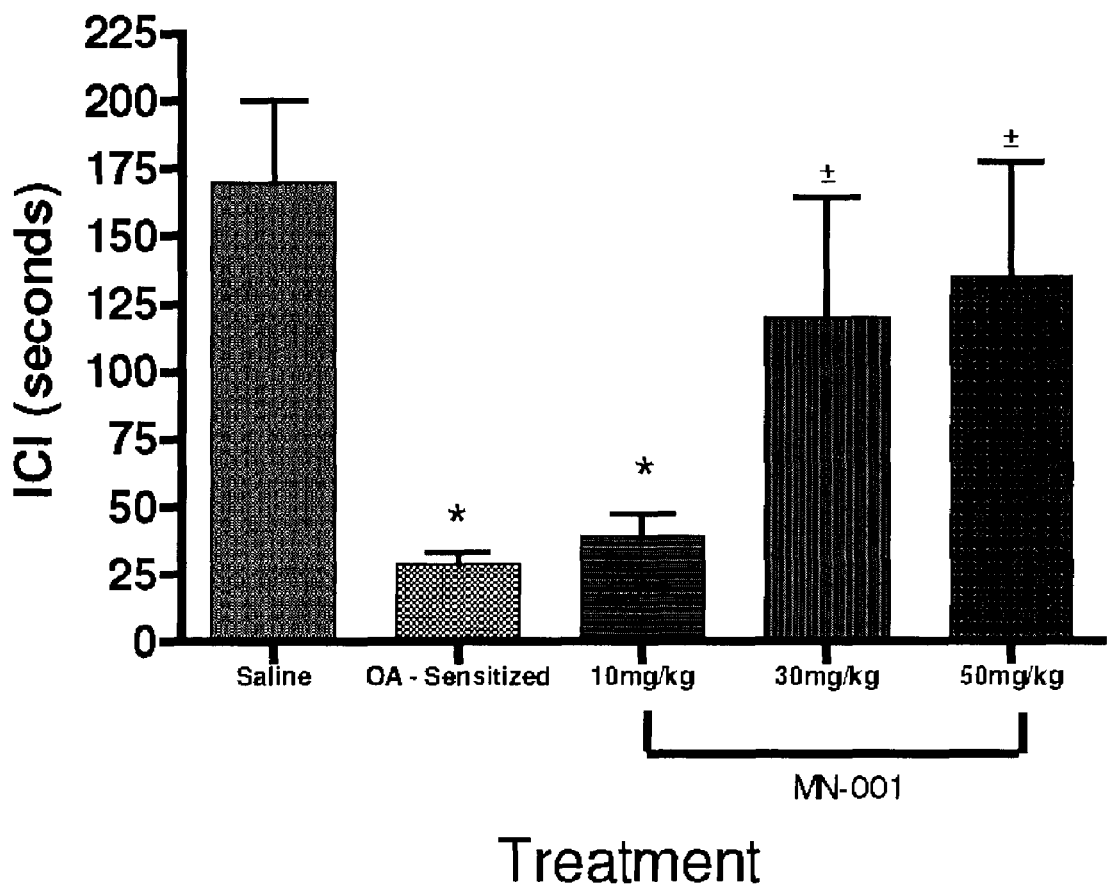
FIG. 4. ICI in control and different treatment groups. An * denotes significance when compared to group 1. A ± denotes significance when compared to group 2.
Figure 5:
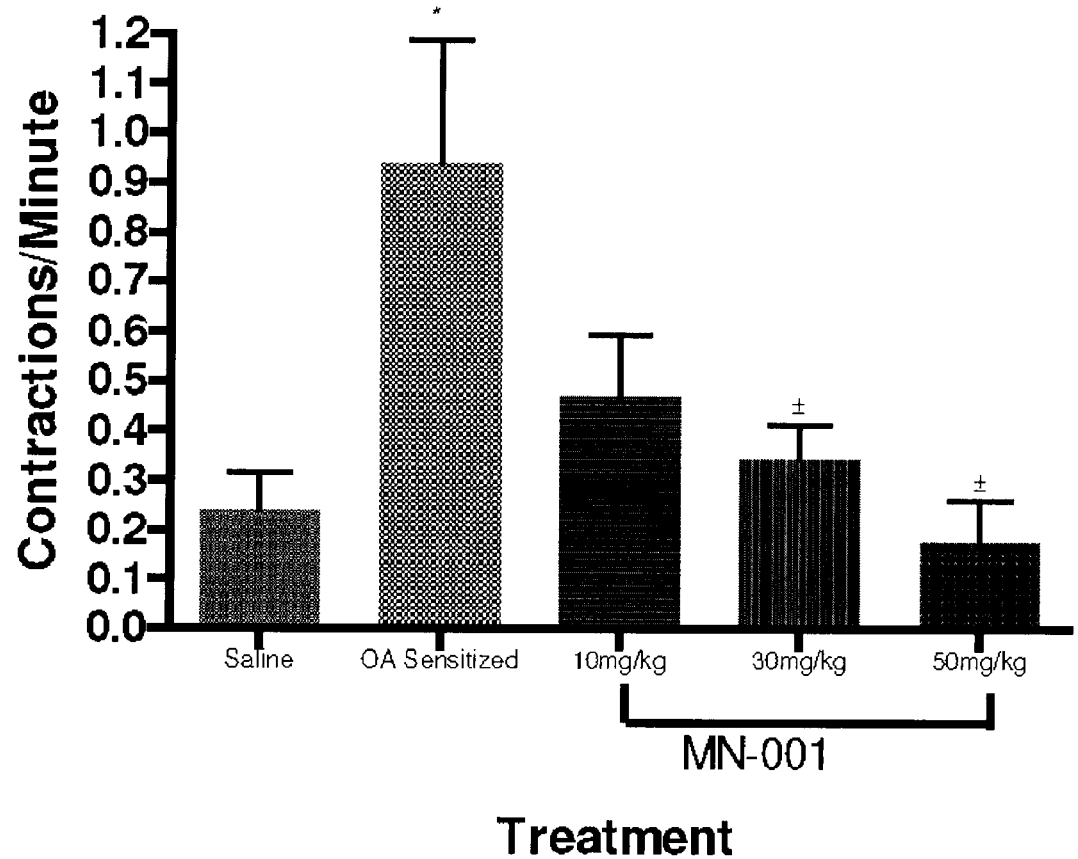
FIG. 5. NVC in control and different treatment groups. An * denotes significance when compared to group 1. A ± denotes significance when compared to group 2.

Results:

Representative tracings of bladder cystometrograms (CMGs) of treatment groups are depicted in FIG. 1A-1E. Infusion of intact rat bladder with 0.9% saline resulted in normal and comparable numbers of voids and NVC (FIG. 1; Table I). In OA sensitized rats, intravesical OA (10 mg/mL) infusion resulted in a significant increase in NVC relative to non-sensitized saline infusion values (FIGS. 1, 3 and 5; Table I). Pre-treatment with Compound 1 resulted in dose-dependent inhibition of OA-induced changes in NVC and ICI (FIGS. 3, 4 and 5; Table I). No significant differences were observed in voiding frequency (FIG. 2) between control (group 1) and different treatment groups (2-5).

CONCLUSIONS

These studies clearly indicate that acute intravesical challenge of OA-sensitized rats causes contractions of bladder smooth muscle leading to a significant increase in NVC and a decrease in ICI. Pre-treatment with 1, preferably at 30 and 50 mg/kg dose levels, produced a significant protection against these OA-induced changes. Similar outcomes are expected with the pre-treatment of Compound 2, a metabolite of 1.

TABLE I

Effect of intravesical ovalbumin on rat bladder before and after treatment with Compound 1

| Agent infused into rat bladder | NVC/minute | Statistical significance* |
|---|---|---|
| Group 1: Sodium Chloride (baseline) (n = 10) | 0.2400 ± 0.07483 | — |
| Group 2: OA (10 mg/mL) (n = 10) | 0.9400 ± 0.2473 | $P < 0.05$ compared to Group 1 |
| Group 3: OA (10 mg/mL) after giving 1 (10 mg/kg) (n = 10) | 0.4700 ± 0.1221 | NS compared to Group 2 |
| Group 4: OA (10 mg/mL) after giving 1 (30 mg/kg) (n = 9) | 0.3444 ± 0.06894 | $P < 0.05$ compared to Group 2 |
| Group 5: OA (10 mg/mL) after giving 1 (50 mg/kg) (n = 9) | 0.1778 ± 0.08296 | $P < 0.05$ compared to Group 2 |

*NS = not significant.

All documents cited herein are incorporated by reference in their entirety. While the invention has been described in detail, and with reference to specific embodiments, it will be apparent to one with ordinary skill in the art that various changes and modifications can be made therein without departing from the spirit and scope of the invention.

The invention claimed is:

1. A method of treating irritable bowel syndrome in a patient suffering therefrom, comprising: administering an effective amount of compound (1)

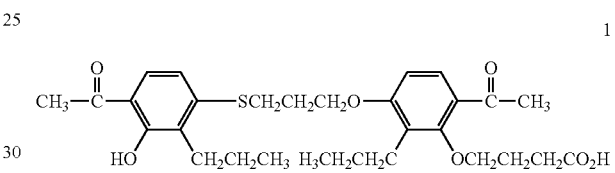

or a pharmaceutically acceptable salt or an ester thereof.

2. The method of claim 1, wherein the compound is administered orally.

3. The method of claim 2, wherein the compound is administered orally in a dosage form that is a tablet or capsule.

4. The method of claim 1, wherein the compound is administered in a liquid.

5. The method of claim 1, wherein the dose is from 250 to 2,500 mg/day, divided into one, two or three portions.

6. The method of claim 1, wherein the compound is present as orthorhombic crystals.

7. The method of claim 1, further comprising administration of compound (2)

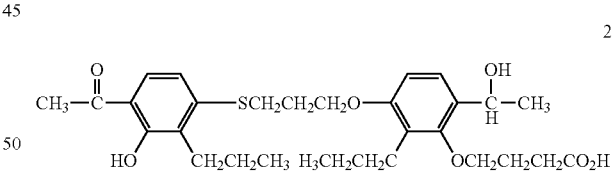

or a pharmaceutically acceptable salt or an ester thereof.

8. A method of treating irritable bowel syndrome in a patient suffering therefrom, comprising: administering an effective amount of compound (2)

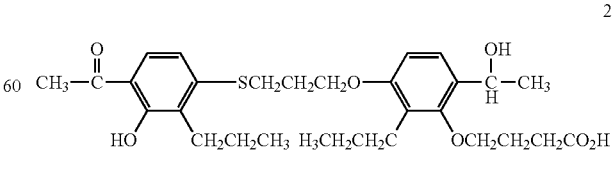

or a pharmaceutically acceptable salt or an ester thereof.

* * * * *